(12) United States Patent  
Epstein

(10) Patent No.: US 11,896,505 B2  
(45) Date of Patent: Feb. 13, 2024

(54) METHODS FOR MAKING AND USING A STRUCTURAL HYDROGEL POLYMER DEVICE

(71) Applicant: Scott M. Epstein, Boston, MA (US)

(72) Inventor: Scott M. Epstein, Boston, MA (US)

(*) Notice: Subject to any disclaimer, the term of this patent is extended or adjusted under 35 U.S.C. 154(b) by 435 days.

(21) Appl. No.: 17/132,493

(22) Filed: Dec. 23, 2020

(65) Prior Publication Data

US 2021/0177630 A1  Jun. 17, 2021

Related U.S. Application Data

(63) Continuation-in-part of application No. 14/881,753, filed on Oct. 13, 2015, now Pat. No. 10,881,537, which is a continuation of application No. 13/231,752, filed on Sep. 13, 2011, now Pat. No. 9,180,028, which is a continuation of application No. 11/590,219, filed on Oct. 31, 2006, now Pat. No. 8,048,350.

(Continued)

(51) Int. Cl.
| | |
|---|---|
| *B29C 41/12* | (2006.01) |
| *A61F 2/844* | (2013.01) |
| *A61F 2/82* | (2013.01) |
| *A61L 29/04* | (2006.01) |
| *A61L 31/04* | (2006.01) |
| *A61L 31/14* | (2006.01) |
| *A61M 25/00* | (2006.01) |
| *A61L 29/14* | (2006.01) |

(52) U.S. Cl.
CPC ............... *A61F 2/844* (2013.01); *A61F 2/82* (2013.01); *A61L 29/041* (2013.01); *A61L 29/145* (2013.01); *A61L 31/048* (2013.01); *A61L 31/145* (2013.01); *A61M 25/0017* (2013.01); *A61M 2207/00* (2013.01)

(58) Field of Classification Search
CPC ....... B29C 97/06; B29C 70/32; B29C 41/085; B29C 14/12
USPC .................................. 264/204, 209.1, 209.2
See application file for complete search history.

(56) References Cited

U.S. PATENT DOCUMENTS

| 3,862,452 A | 1/1975 | Wichterle et al. |
| 3,890,683 A | 6/1975 | Vodnansky et al. |

(Continued)

FOREIGN PATENT DOCUMENTS

| WO | 2000018446 A1 | 4/2000 | |
| WO | WO-0018446 A1 * | 4/2000 | ........... A61L 29/085 |

OTHER PUBLICATIONS

W.K. Wan et al., "Optimizing the Tensile properties of Polyvinyl Alcohol Hydrogel for the Construction of a Bioprosthetic Heart Valve Stent", J Biomed Mater Res (Appl Biomater) 2002, 63, 854-861.

*Primary Examiner* — Cachet I Proctor  
(74) *Attorney, Agent, or Firm* — Intrinsic Law Corp.

(57) ABSTRACT

The present invention relates generally a manufacturing process which results in a completely hydrogel polymer device that maintains lumen patency which allows for numerous applications. One or more physical post-implantation dimensions of the device can be controlled by placing it in a solution that has a predetermined osmolarity and/or pH. In addition, the device can deliver an absorbed therapeutic agent to a target anatomical site. Alternatively, the device can function as a selective membrane to selectively absorb one or more target molecules from a body fluid.

12 Claims, 21 Drawing Sheets

Related U.S. Application Data

(60) Provisional application No. 60/731,740, filed on Oct. 31, 2005.

(56) References Cited

U.S. PATENT DOCUMENTS

| | | | |
|---|---|---|---|
| 4,026,296 A * | 5/1977 | Stoy | A61L 29/041 |
| | | | 128/207.15 |
| 4,183,884 A | 1/1980 | Wichterle et al. | |
| 4,475,972 A | 10/1984 | Wong | |
| 4,762,128 A | 8/1988 | Rosenbluth | |
| 4,943,618 A | 7/1990 | Stoy et al. | |
| 5,149,052 A | 9/1992 | Stoy et al. | |
| 5,258,042 A * | 11/1993 | Mehta | A61L 31/048 |
| | | | 623/921 |
| 5,601,881 A | 2/1997 | Grimm et al. | |
| 6,039,694 A | 3/2000 | Larson et al. | |
| 6,060,534 A | 5/2000 | Ronan et al. | |
| 6,200,257 B1 | 3/2001 | Winkler | |
| 6,368,356 B1 | 4/2002 | Zhong et al. | |
| 6,488,802 B1 | 12/2002 | Evingston et al. | |
| 6,500,375 B1 * | 12/2002 | Aulick | B29C 41/085 |
| | | | 118/118 |
| 6,547,908 B2 | 4/2003 | Keyes et al. | |
| 2002/0143385 A1 | 10/2002 | Yang | |
| 2002/0156342 A1 | 10/2002 | Burton et al. | |
| 2003/0021762 A1 | 1/2003 | Luthra et al. | |
| 2003/0211130 A1 | 11/2003 | Sanders et al. | |
| 2003/0222369 A1 | 12/2003 | Nicora et al. | |
| 2005/0159704 A1 | 7/2005 | Scott et al. | |
| 2006/0052478 A1 | 3/2006 | Madsen et al. | |
| 2007/0073402 A1 * | 3/2007 | Vresilovic | A61F 2/441 |
| | | | 264/331.19 |

* cited by examiner

STEP 1.0

STEP 2.0

1800

| Table 1.0 Change device saturated with specific solutions exhibits when placed in solution |||
|---|---|---|
| Device saturated pH (5.5 to 7.0) Volume of stent ~ approximate 2.0 cc aqueous volume | Saturated device placed in pH (5.5 to 7.0) equilibrium % concentration and time to are function of volume placed into | Change |
| Distilled water | Di-water | No change |
| 0.9% saline | | Swell |
| 3.5% saline | | Swell |
| 5.0% saline | | Swell |
| Distilled water | 0.9% saline | Shrink |
| 0.9% saline | | No change |
| 3.5% saline | | Swell |
| 5.0% saline | | Swell |
| Distilled water | 5.0% saline | Shrink |
| 0.9% saline | | Shrink |
| 3.5% saline | | Shrink |
| 5.0% saline | | No change |
| Distilled water | Urine Low / normal osmolarity, low / normal density, low / normal concentration of elements and compounds | Shrink |
| 0.9% saline | | Swell |
| 3.5% saline | | Swell |
| 5.0% saline | | No change |
| Distilled water | Urine High osmolarity, high density, high concentration of elements and compounds | Shrink |
| 0.9% saline | | Shrink |
| 3.5% saline | | No change |
| 5.0% saline | | Swell |
| Distilled water | Blood High osmolarity, high density, high concentration of elements and compounds | Shrink |
| 0.9% saline | | Shrink |
| 3.5% saline | | No change |
| 5.0% saline | | Swell |
| Distilled water | Blood Low / normal osmolarity, low / normal density, low / normal concentration of elements and compounds | Shrink |
| 0.9% saline | | No change |
| 3.5% saline | | Swell |
| 5.0% saline | | Swell |
| Basic solution pH (>) 7.0 | Acidic solution pH (<) 7.0 | Shrink |
| Acidic solution pH (<) 7.0 | Basic solution pH (>) 7.0 | Swell |
| Distilled water | (blood) high % glucose | Shrink |
| 0.9% saline | | Shrink |
| 3.5% saline | | No change |
| 5.0% saline | | No change |
| Distilled water | Normal (urine) high % Calcium Oxalate | Shrink |
| 0.9% saline | | Shrink |
| 3.5% saline | | Swell |
| 5.0% saline | | Swell |

FIG. 18

METHODS FOR MAKING AND USING A STRUCTURAL HYDROGEL POLYMER DEVICE

CROSS-REFERENCE TO RELATED APPLICATIONS

This application is a continuation-in-part of U.S. patent application Ser. No. 14/881,753, filed on Oct. 13, 2015, which is a continuation of U.S. patent application Ser. No. 13/231,752, filed on Sep. 13, 2011, now U.S. Pat. No. 9,180,028, which is a continuation of U.S. patent application Ser. No. 11/590,219, filed on Oct. 31, 2006, now U.S. Pat. No. 8,048,350, which claims priority to U.S. Provisional Application No. 60/731,740, filed on Oct. 31, 2005, which are incorporated herein by reference.

FIELD OF INVENTION

The present invention relates generally to a manufacturing process and a resulting apparatus which results in a completely hydrogel polymer device that maintains lumen patency which allows for numerous medical device applications, such as catheters, stents, solid shapes, profiles, slugs, plugs, self-closing cylinders, etc.

BACKGROUND OF THE INVENTION

Generally, the common approaches utilized in the art to fabricate a product from hydrolyzed PAN entail typically coagulating a single layer or heavily plasticizing a solvent based formula hydrolyzed PAN, in order that it may be molded or extruded by conventional thermoplastic extrusion or injection molding methods. Unfortunately, do to limitations, these materials and related processes are not reliable and often lead to inconsistencies in production and/or components.

As referenced in U.S. Pat. No. 6,232,406 and in fact improvements so noted in U.S. Pat. No. 4,943,618 are probably not necessary when manufacturing a product with the disclosed process. Many types of devices are available and generally well known in the art of catheter design and construction which exhibit various curved and coiled end geometrical configurations for anchorage while others rely on material and polymer characteristics to increase performance and patient comfort. it is also generally known that some devices can be particularly difficult to implant, and withdraw. Unfortunately these designs do not minimize migrations and their lubricous coatings, which will erode off, do not diminish patient comfort, and encrustation.

In a typical modality, conventional thermoplastic polyurethane Ureteral Stent or Catheter is likely to migrate due to physiological or peristaltic organ and or muscle movement. Thereafter the device may become dislodged from its location rendering it ineffective. Additionally, after a relatively short period of time urine salts for example typically adhere to the coated and uncoated devices diminishing flow, and comfort, increasing patient pain and jeopardizing device integrity. The disclosed invention will alleviate these unacceptable complications.

SUMMARY OF INVENTION

It is an object of the invention to provide a stent or catheter fabricated in a manner totally comprised of a hydrogel capable of becoming structural in its final configuration having a cross sectional area that increases with hydration, while maintaining mechanical integrity.

It is a further object of the invention to provide a catheter or stent that incorporates a manufacturing process that results in an end product that is stable, will not erode and will exhibit tensile strengths and elongations that allow use in applications where typical thermoplastic devices are currently used. Said devices immediately exhibit lubricous surface characteristics when wetted with any aqueous media and provide increased resistance to biological complications once implanted. Substantial mechanical characteristics are exhibited by a fully hydrated device, which can be loaded with colorants, radiopacifiers and fillers.

The present invention relates generally to the field of catheters used to maintain flow in the urinary system for example and in particular a configuration that maintains an atraumatic passage where the structural hydrogel composition provides comfort, placement and mechanical advantage. Hydrolyzed polyacrylicnitrile (PAN) polymers produced utilizing the present method result in a superior end product when produced with the disclosed process. Use of this method overcomes inconstancies in present formulations and devices made in accordance with the instant process yield a 100% hydrogel composition stent, catheter or hybrid version which may can be implanted with a substantially smaller diameter and then hydrated into a predictable larger, softer size within a controllable period of time. The catheter or hybrid will also be relatively rigid for ease of placement and track-ability.

The present invention relates generally to a manufacturing process which results in a completely hydrogel polymer device that maintains lumen patency which allows for numerous applications. Catheters and stems are particular examples, and their composition, mechanical characteristics, and the significantly unique ability to conduct and allow fluids to pass from one end to the other without physiological rejection, inflammation, or manifestation of complications due to implant or otherwise undesirable outcomes when used for ambulatory and or therapeutic interventions is the purpose of the invention.

Accordingly, a ureteral stent is provided having anchorage that will not migrate, exhibits resistance to encrustation and facilitates ease of implant and withdrawal. In general, the placement of the structural hydrogel, ureteral stent or catheter creates in a path from which fluids can he reliably conducted from one end to the other, which requires no significant clinical follow up due to device migration, encrustation or related patient comfort issues.

An aspect of the invention is directed to a method for manufacturing a medical device, comprising: depositing an inner layer material comprising a hydrogel on a rotating, horizontally-disposed mandrel; coagulating the inner layer comprising the hydrogel in place on the mandrel; dehydrating the inner layer material; depositing a second layer of material comprising a hydrogel on the inner layer such that the medical device is produced without thermoplastic processing; and placing the medical device in a solution having a predetermined osmolarity.

In one or more embodiments, the predetermined osmolarity is approximately equal to an osmolarity of a target body fluid, whereby one or more physical dimensions of the medical device remains about the same after the medical device is implanted in a target anatomical site that includes the target body fluid. In one or more embodiments, the solution comprises a hypertonic saline solution. In one or more embodiments, the hypertonic saline solution has an NaCl concentration is in a range of about 3.5% NaCl to about 4% NaCl. In one or more embodiments, the target body fluid comprises urine.

In one or more embodiments, the one or more physical dimensions comprises an outer diameter of the medical device. In one or more embodiments, the predetermined osmolarity is greater than an osmolarity of a target body fluid, whereby one or more physical dimensions of the medical device increases after the medical device is implanted in a target anatomical site that includes the target body fluid. In one or more embodiments, the solution comprises a hypertonic saline solution having an NaCl concentration in a range of about 4% NaCl to about 5% NaCl. In one or more embodiments, the one or more physical dimensions comprises an outer diameter of the medical device, and the outer diameter increases by about 20% to about 30% after the medical device is implanted in the target anatomical site compared to the outer diameter immediately before the medical device is implanted in the target anatomical site.

In one or more embodiments, the predetermined osmolarity is lower than an osmolarity of a target body fluid, whereby one or more physical dimensions of the medical device decreases after the medical device is implanted in a target anatomical site that includes the target body fluid. In one or more embodiments, the solution comprises a saline solution having an NaCl concentration in a range of about 0.1% NaCl to about 2.5% NaCl. In one or more embodiments, the one or more physical dimensions comprises an outer diameter of the medical device, and the outer diameter decreases by about 20% to about 30% after the medical device is implanted in the target anatomical site compared to the outer diameter immediately before the medical device is implanted in the target anatomical site.

Another aspect of the invention is directed to a method comprising depositing an inner layer material comprising a hydrogel on a rotating, horizontally-disposed mandrel; coagulating the inner layer comprising the hydrogel in place on the mandrel; dehydrating the inner layer material; depositing a second layer of material comprising a hydrogel on the inner layer such that the medical device is produced without thermoplastic processing; placing the medical device in a liquid that includes a therapeutic agent; and absorbing the therapeutic agent in the medical device.

In one or more embodiments, the method further comprises implanting the medical device in a target anatomical site; and releasing at least some of the absorbed therapeutic agent in the medical device to the target anatomical site. In one or more embodiments, the therapeutic agent includes a drug. In one or more embodiments, the drug includes a chemotherapy drug.

Yet another aspect of the invention is directed to a method comprising forming a medical device that comprises: an inner layer including a coagulated hydrogel polymer material defining a lumen of the medical device; and one or more additional layers encircling the inner layer, a first of the one or more additional layers including a coagulated hydrogel polymer material fused with the underlying coagulated hydrogel polymer material of the inner layer at an interface; the interface having a structural configuration corresponding to the hydrogel polymer material of the inner layer in a dehydrated state fused to the coagulated hydrogel polymer material of the first additional layer in a solvated state. The coagulated hydrogel polymer material of the inner layer and the coagulated hydrogel polymer material of the first of the one or more additional layers encircling the inner layer are structurally stable so that the medical device does not require a substrate or scaffold to maintain its mechanical characteristics. The medical device functions as a selective membrane that selectively absorbs a target molecule. The method further comprises placing the medical device in a body fluid at a target anatomical site, the body fluid including the target molecule; and selectively absorbing the target molecule from the body fluid with the medical device.

In one or more embodiments, the body fluid comprises urine and the target molecule comprises calcium oxalate.

Another aspect of the invention is directed to a medical treatment comprising: placing a medical device in a target anatomical site, the medical device comprising: an inner layer including a coagulated hydrogel polymer material defining a lumen of the medical device; and one or more additional layers encircling the inner layer, a first of the one or more additional layers including a coagulated hydrogel polymer material fused with the underlying coagulated hydrogel polymer material of the inner layer at an interface; the interface having a structural configuration corresponding to the hydrogel polymer material of the inner layer in a dehydrated state fused to the coagulated hydrogel polymer material of the first additional layer in a solvated state. The coagulated hydrogel polymer material of the inner layer and the coagulated hydrogel polymer material of the first of the one or more additional layers encircling the inner layer are structurally stable so that the medical device does not require a substrate or scaffold to maintain its mechanical characteristics. The medical device is in a dehydrated or a partially-hydrated state. The medical device has a target profile when it transitions to a fully-hydrated state. The method further comprises absorbing a target body fluid with the medical device; transitioning the medical device to the fully-hydrated state, wherein in the fully-hydrated state: one or more physical dimensions of the medical device is/are increased when the medical device is in the fully-hydrated state compared to when the medical device is in the dehydrated or the partially-hydrated state, and the medical device conforms to the target profile.

In one or more embodiments, the target anatomical site is the brain and the target body fluid comprises blood.

BRIEF DESCRIPTION OF THE DRAWINGS

Advantages of the present invention will be apparent from the following detailed description of exemplary embodiments thereof, which description should be considered in conjunction with the accompanying drawings, in which:

FIG. 3, step (2) discloses the basic function of the process thereafter step (1) whereby concurrent layers fuse together;

inherently due to for example the solvent concentration in the concurrent outer layer and effect on the inner first layer now dehydrated for proceeding with step (2). Additionally, when and where required an adhesive can be absorbed by the dehydrated layer and or preloaded into the concurrent layer which would be extremely valuable when applying the hydrogel to other dissimilar surfaces.

Figure 4A:
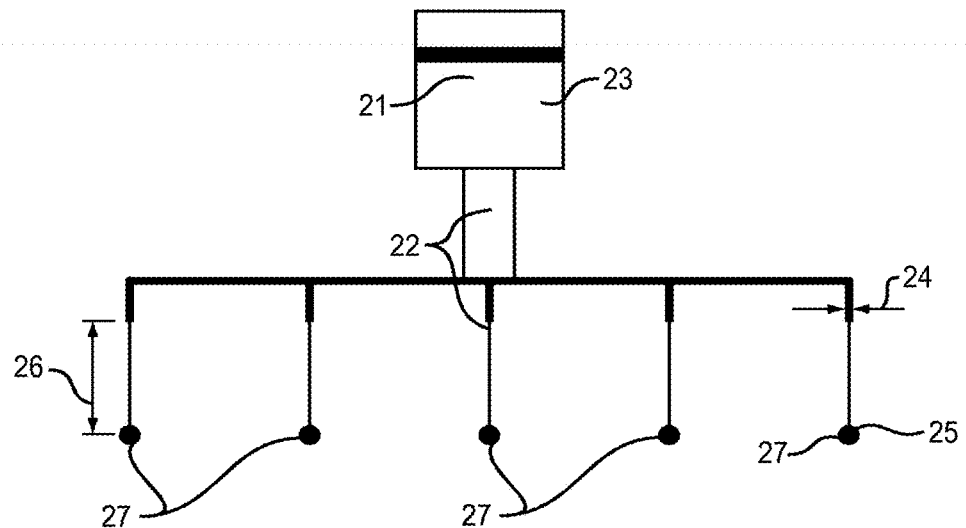
Figure 4B:
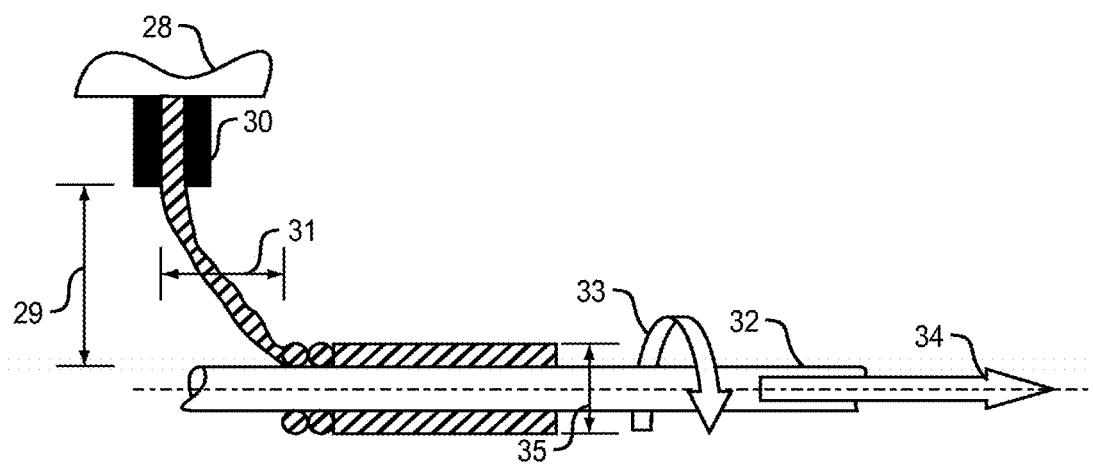
Figure 4C:
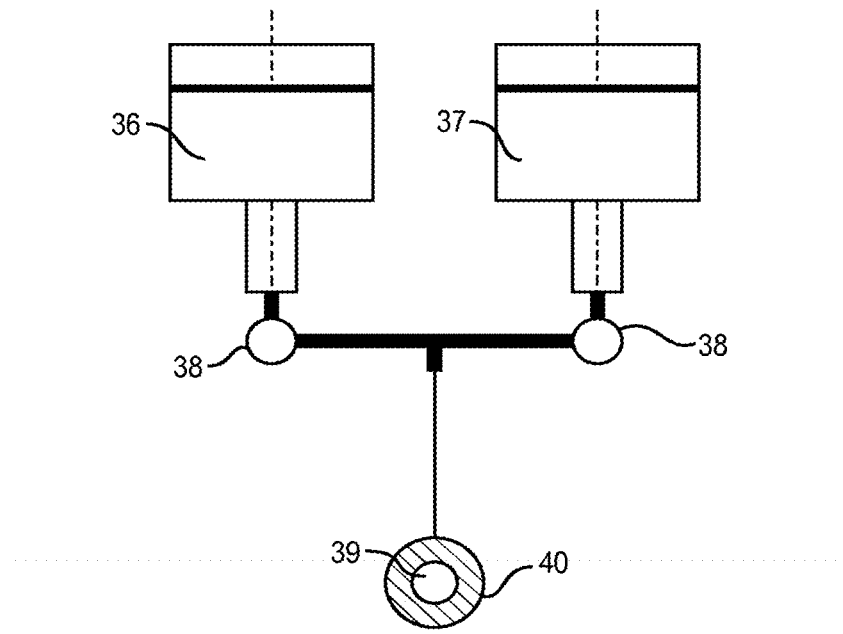

FIG. 4A, a front view, 4B, a side view, 4C a rear view & 4D, the opposing side view disclose and details the aspects of the process. FIGS. 4A & B specifically exhibit that multiple devices can be produced simultaneously whereby hydrogel in a semi-fluid form of a specific viscosity is pumped or otherwise transported thru a manifold and out an orifice of specific size, at a specific temperature and flow rate. Additionally FIGS. 4A & B show that in setting up the process configuration, mandrel size, distance from the manifold outlet and mandrel speed both in RPM and in line speed is coordinated to the aforementioned hydrogel characteristics. FIGS. 4C & D further identifies variations in the process whereby multiple materials can be deployed in a single process yielding one product with several materials included.

Figure 5A:
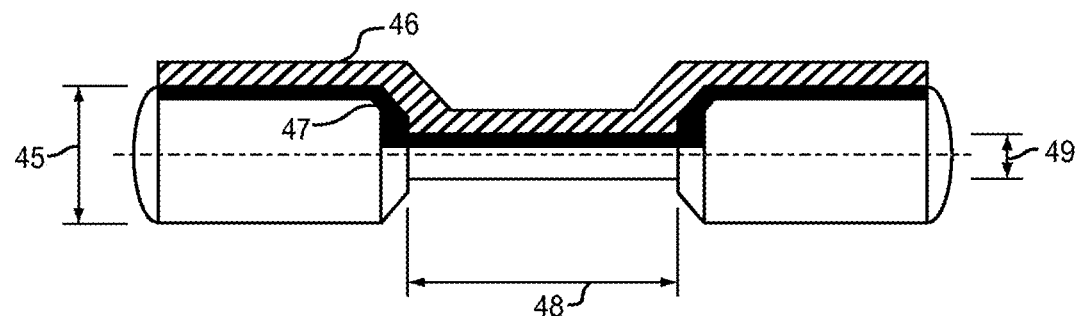

FIGS. 5A & B discloses aspects of the process whereby, mandrel design and specification can be modified in many ways contributing to end product design and performance criteria and characteristics. For example, instead of a straight uniform mandrel, FIG. 5A indicates a "barbell" shaped mandrel that allows for an as cast profile in process whereby the deposition of hydrogel conformingly coats the mandrel in process.

Figure 5B:
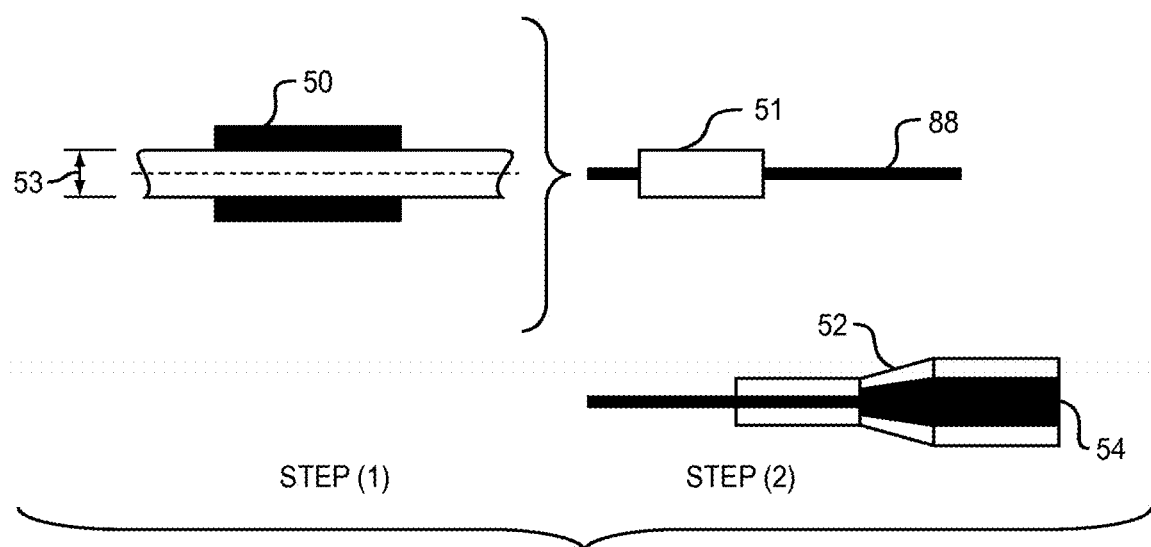

FIG. 5B discloses a method for enhancing density and or product characteristics for example by removing dehydrated deposition from mandrel in step and transferring to either a small mandrel whereby add tonal layers may exhibit greater potential compression, become denser, effect dug delivery or wicking gradients and or provide different elongation than otherwise in the same or other devices of same or similar material. Similarly, a dehydrated deposition can be transferred to a larger mandrel for further modification in process. In this manner a hydrated deposition can be dehydrated onto the larger mandrel and processed further thereafter.

Figure 6:
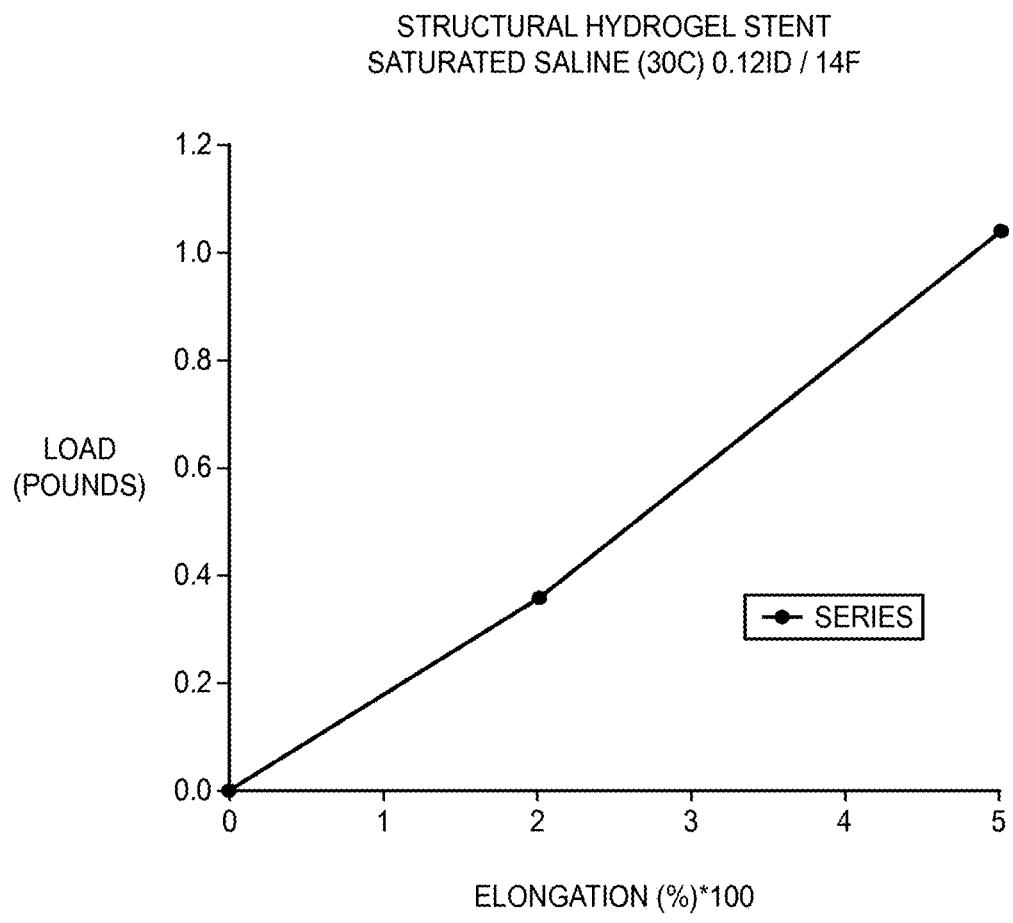

FIG. 6 is a stress/strain graph of a sample processed in accordance with the disclosed process. The low load with respect to high elongation is demonstrated.

Figure 7A:
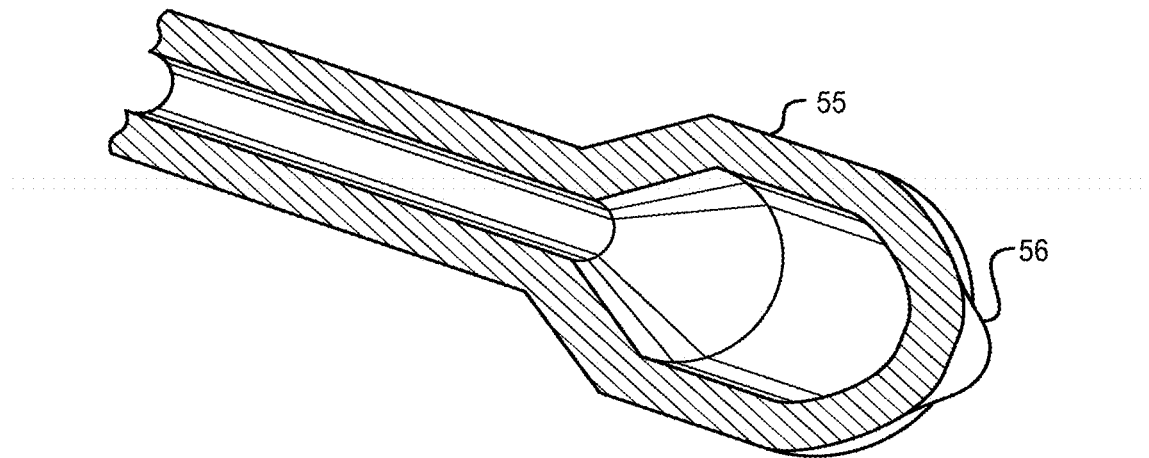

FIGS. 7A, B, C, D, E, F & G are examples of Hybrid compositions that are possible due to the disclosed process.

Figure 8A:
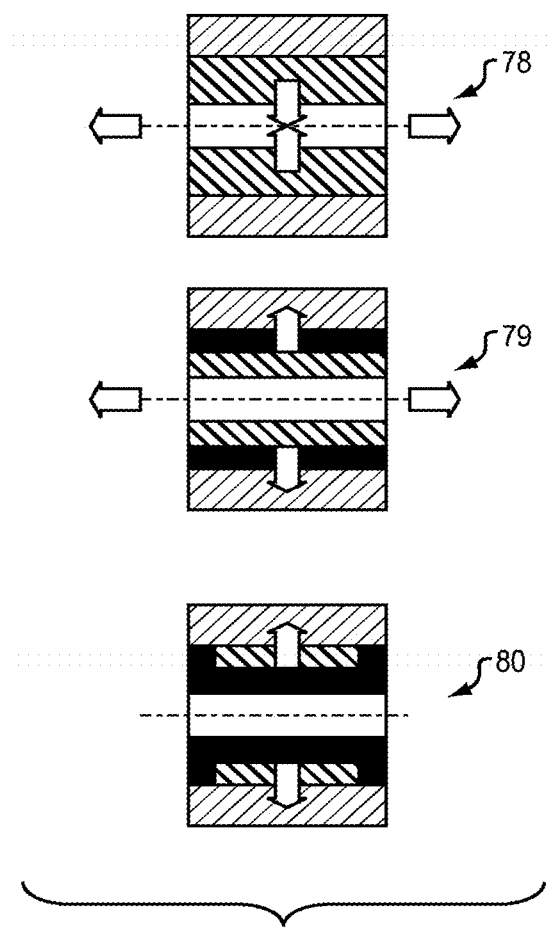

FIGS. 8A & B are examples of compositions that are possible due to the disclosed process whereby force and aqueous gradients maybe directed.

Figure 9A:
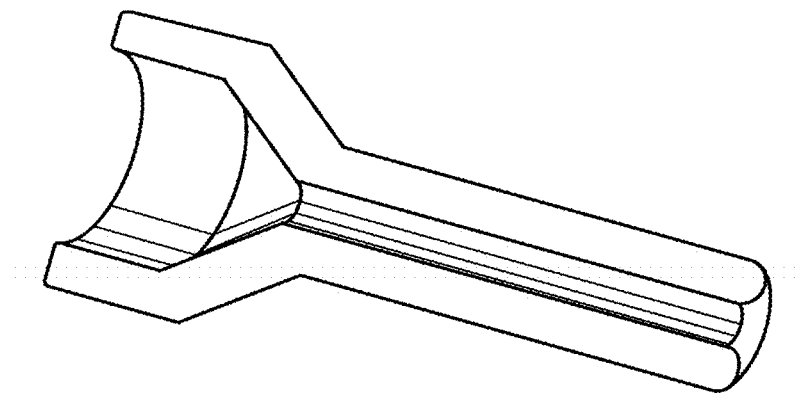
Figure 9B:
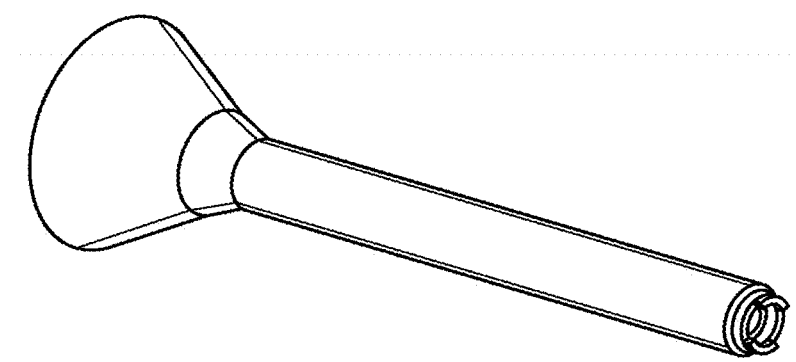

FIGS. 9A & 9B are configurations of a stent or catheter consistent with the present invention; showing a predominant longitudinal representation and views of anchorage methods at corresponding ends. Said anchorage may be but are not limited to barbell, or trumpet profiles at one or both ends of a device.

Figure 10:
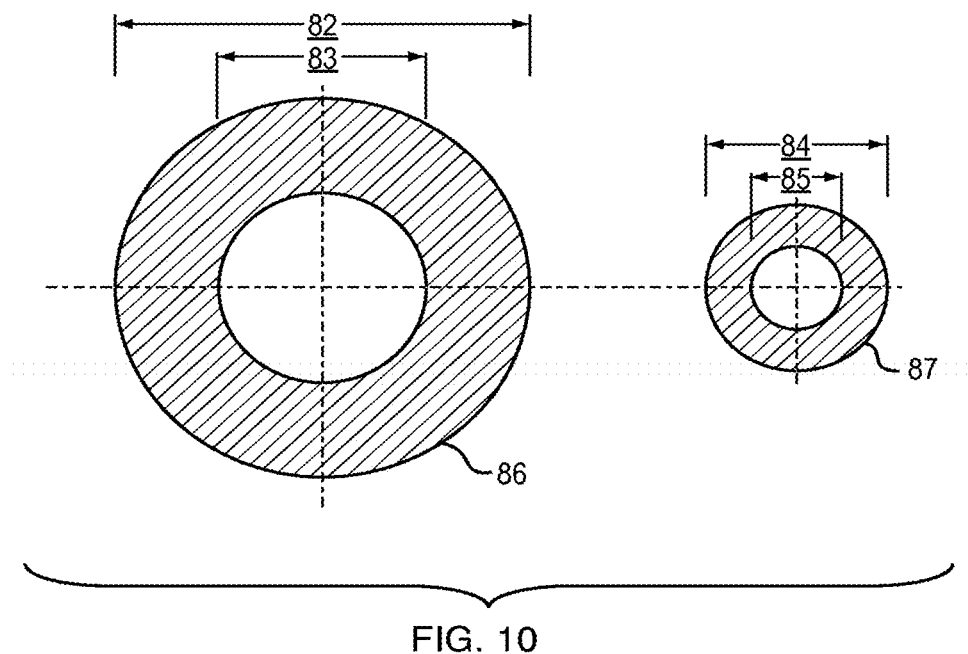

FIG. 10 is a section according to the invention illustrated to show the change in annular cross sectional area that can be expected proportional to the volume of fluid absorbed.

Figure 11:
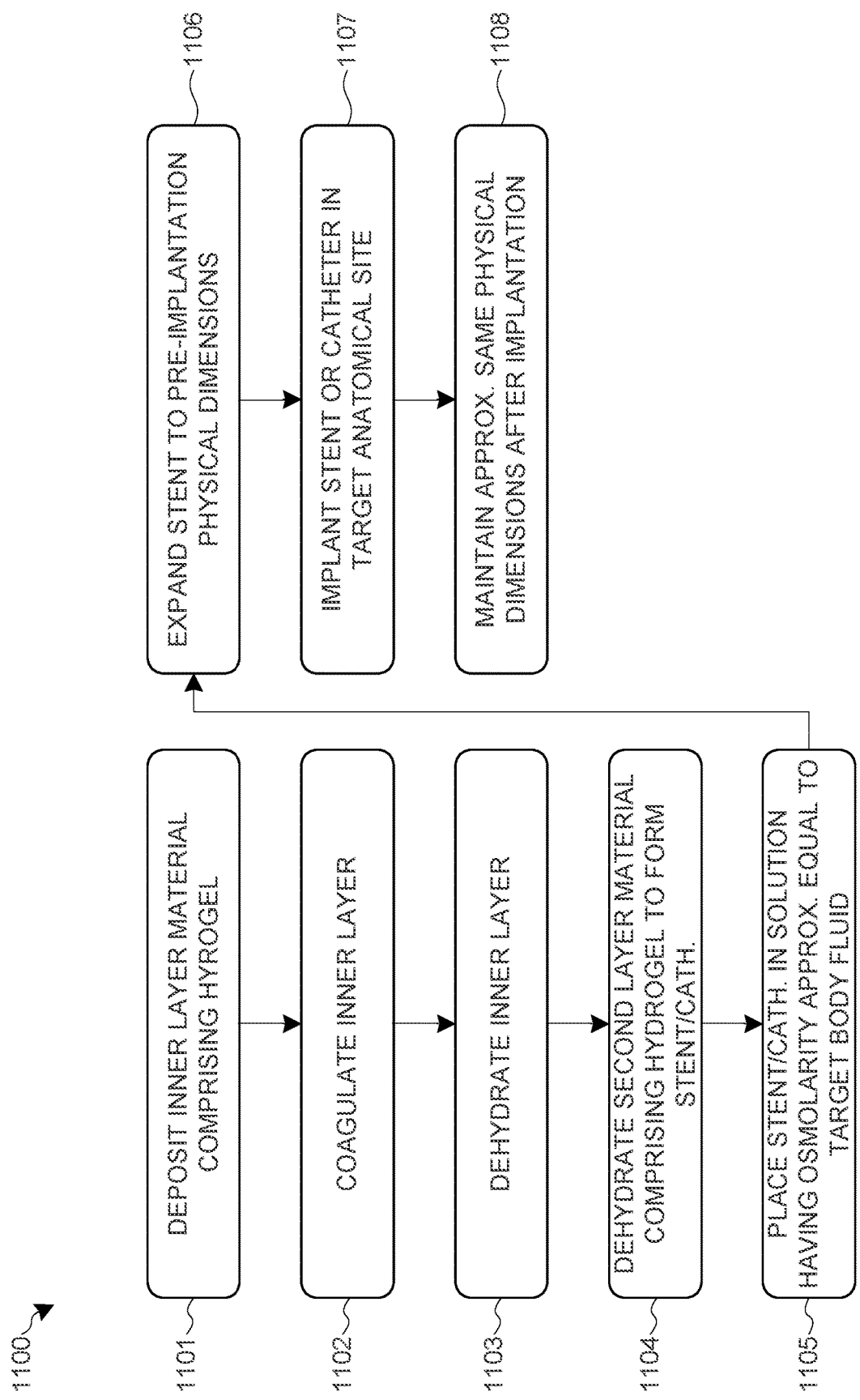

FIG. 11 is a flow chart of a method for manufacturing a medical device according to an embodiment.

Figure 12:
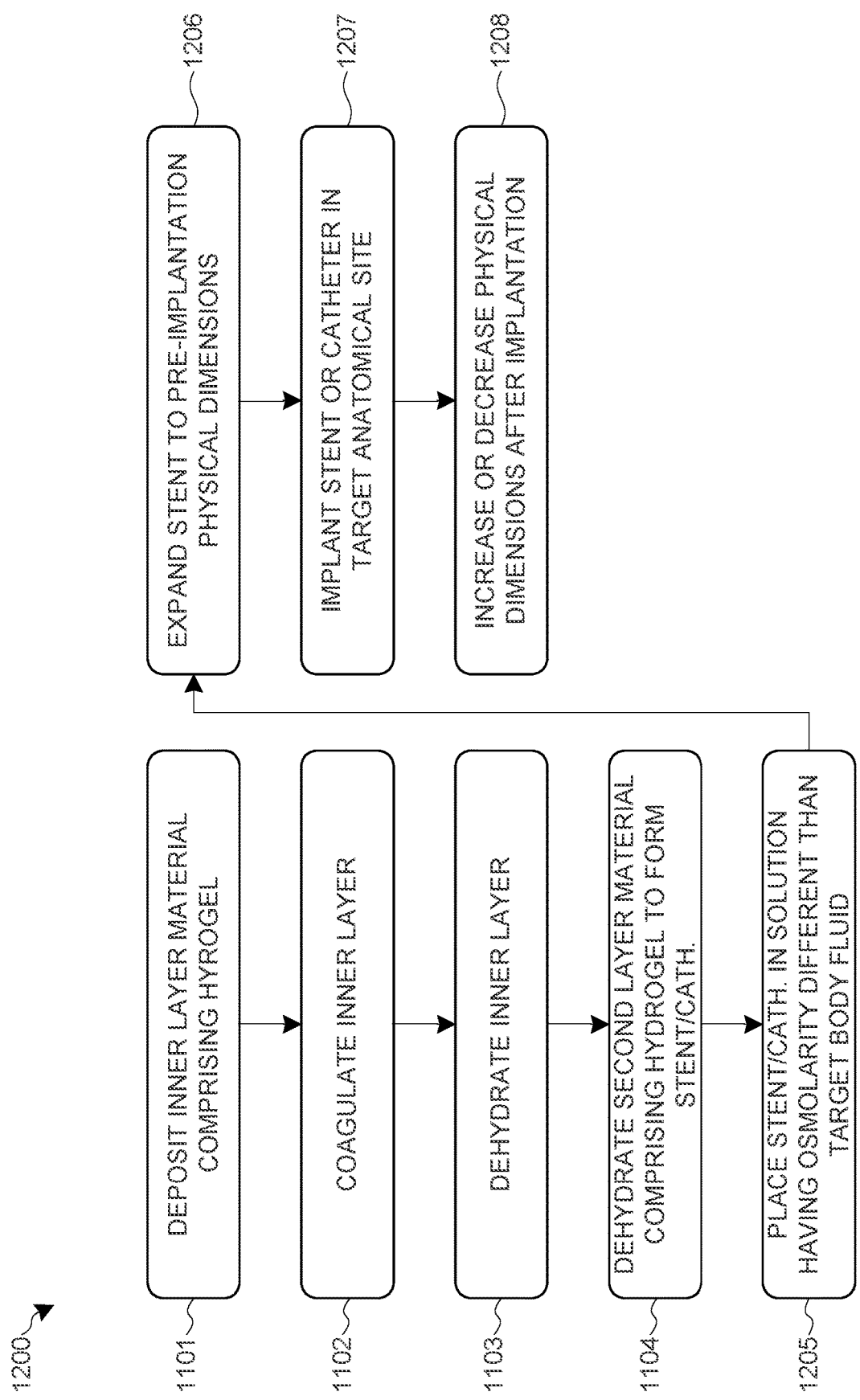

FIG. 12 is a flow chart of a method for manufacturing a medical device according to another embodiment.

Figure 13:
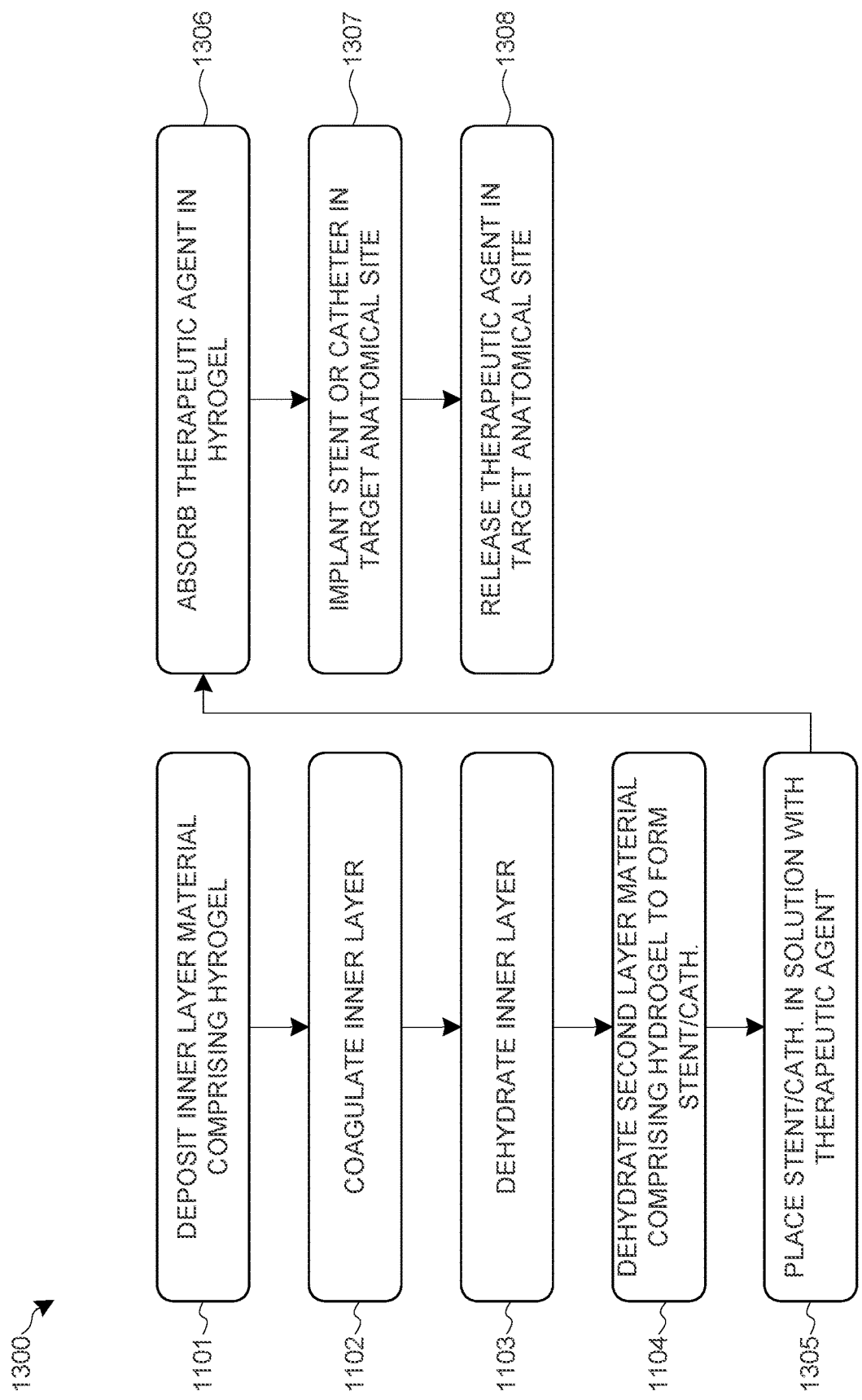

FIG. 13 is a flow chart of a method for manufacturing a medical device according to another embodiment.

Figure 14:
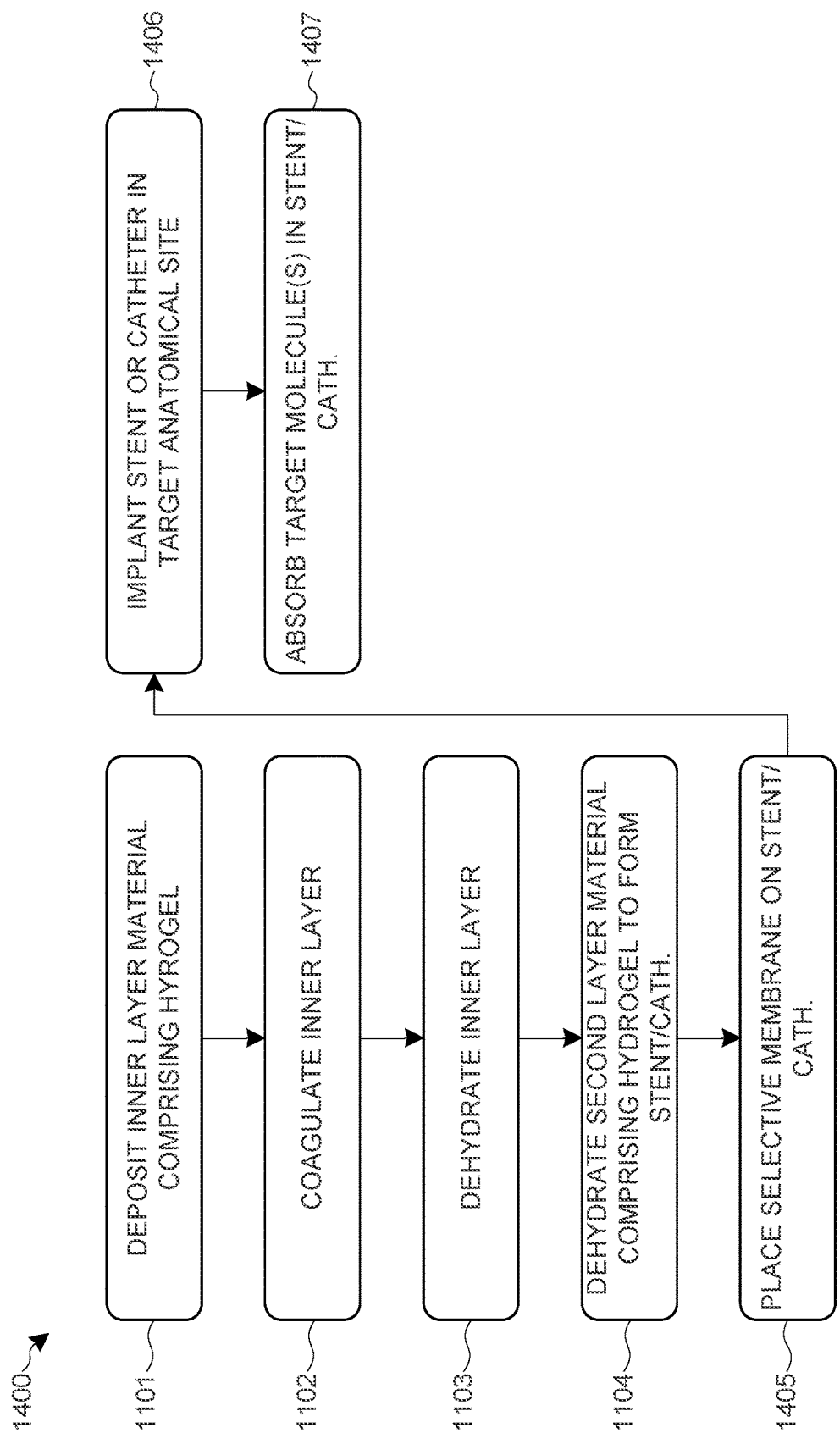

FIG. 14 is a flow chart of a method for manufacturing a medical device according to another embodiment.

Figure 15:
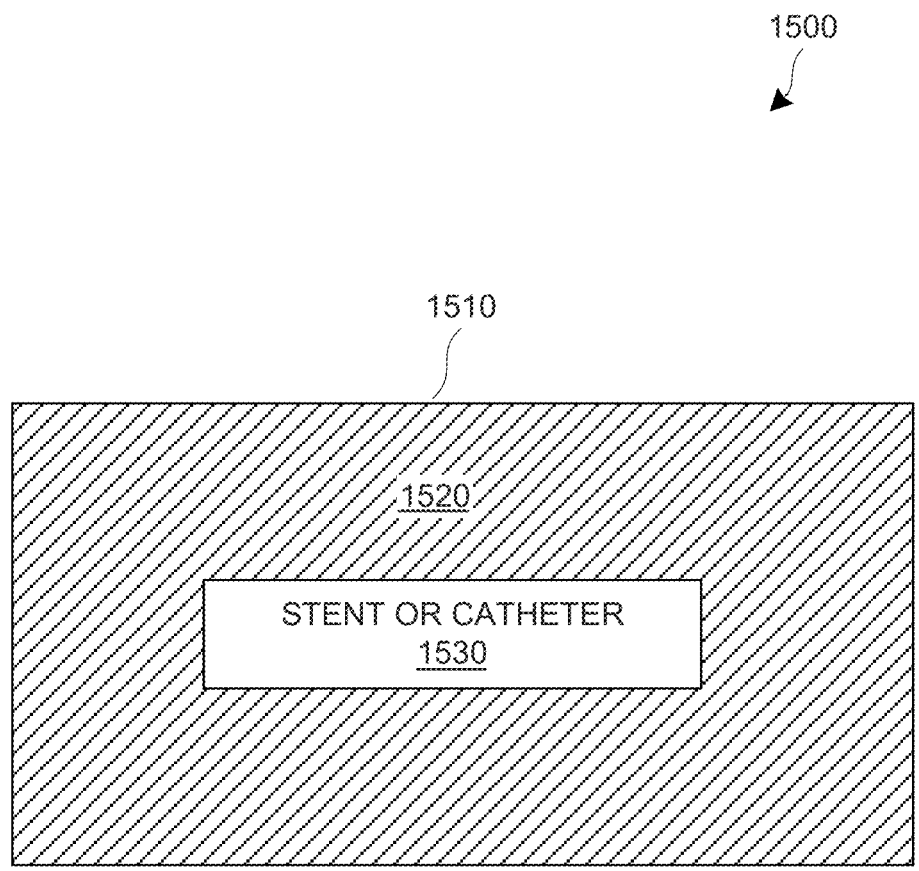

FIG. 15 is a block diagram of an apparatus for manufacturing a medical device according to an embodiment.

Figure 16:
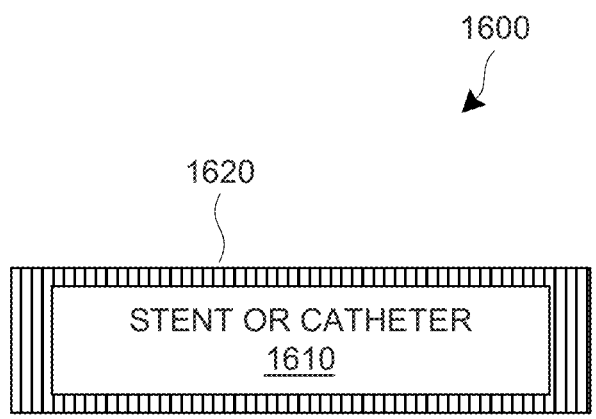

FIG. 16 is a block diagram of a medical device that can selectively-absorb one or more target molecules according to an embodiment.

Figure 17A:
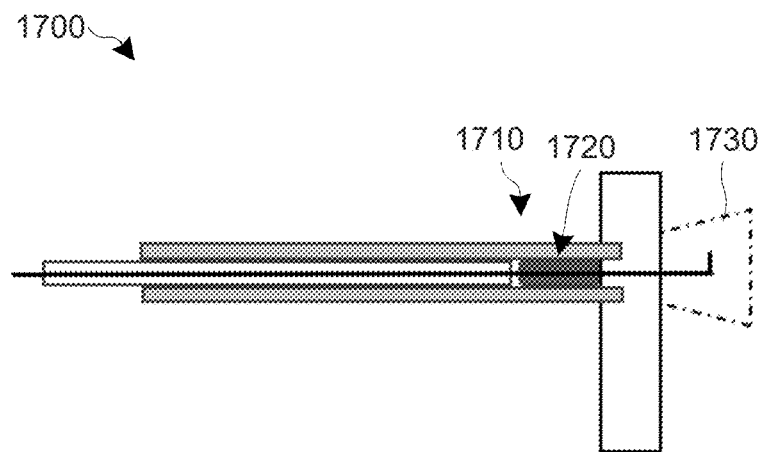

FIG. 17A illustrates an implanted medical device in a dehydrated or partially-hydrated state.

Figure 17B:
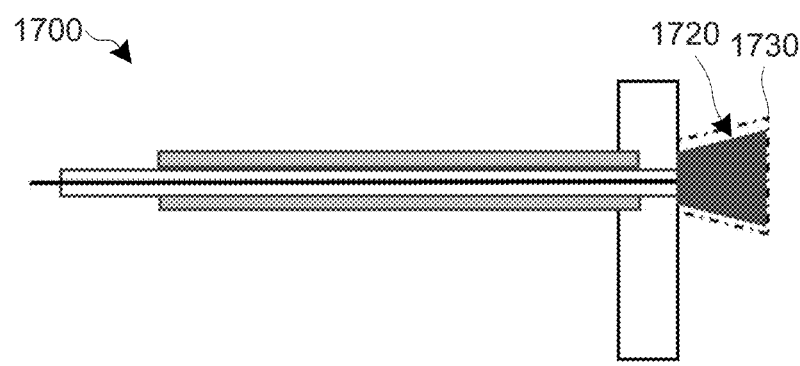

FIG. 17B illustrates the implanted medical device after it has hydrated (e.g., in a fully-hydrated state).

FIG. 18 is an example table of the change in physical dimensions of the medical device when it is pre-treated in a first solution having a first osmolarity and then placed in a second solution having a second osmolarity.

DETAILED DESCRIPTION OF PREFERRED EMBODIMENTS

A stent, catheter, plug or composite of the structural hydrogel and a metal, plastic or other component, and process for producing the same is illustrated herein. The finished device as disclosed is comprised of 100% Hydrogel polymer which is stable and structural in its final composition, not requiring a substrate or scaffold to maintain composition or mechanical characteristics.

Figure 1:
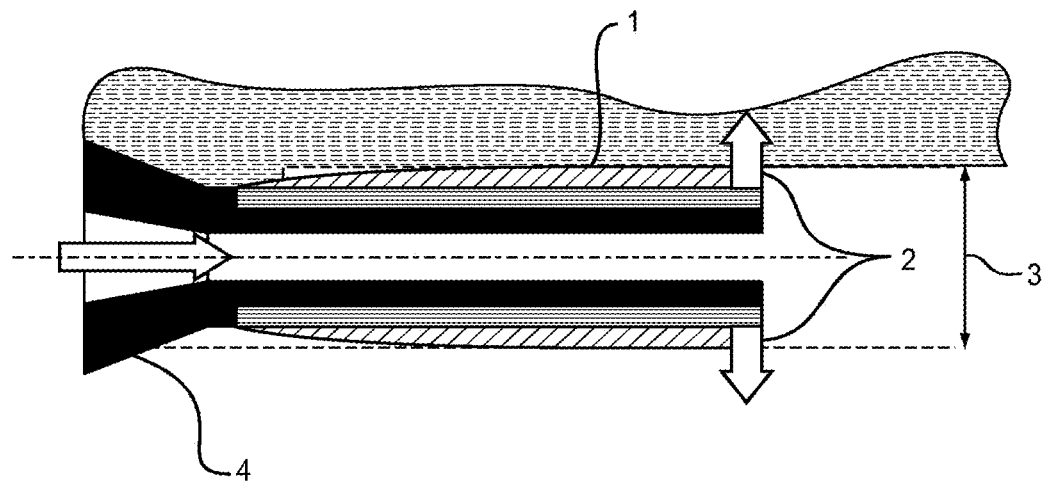
FIG. 1 is a configuration of a stent or catheter consistent with the present invention, showing a predominant longitudinal representation and views of anchorage methods at corresponding ends. Said anchorage may be but are not limited to barbell, or trumpet profiles at one or both ends of a device.
Figure 2:
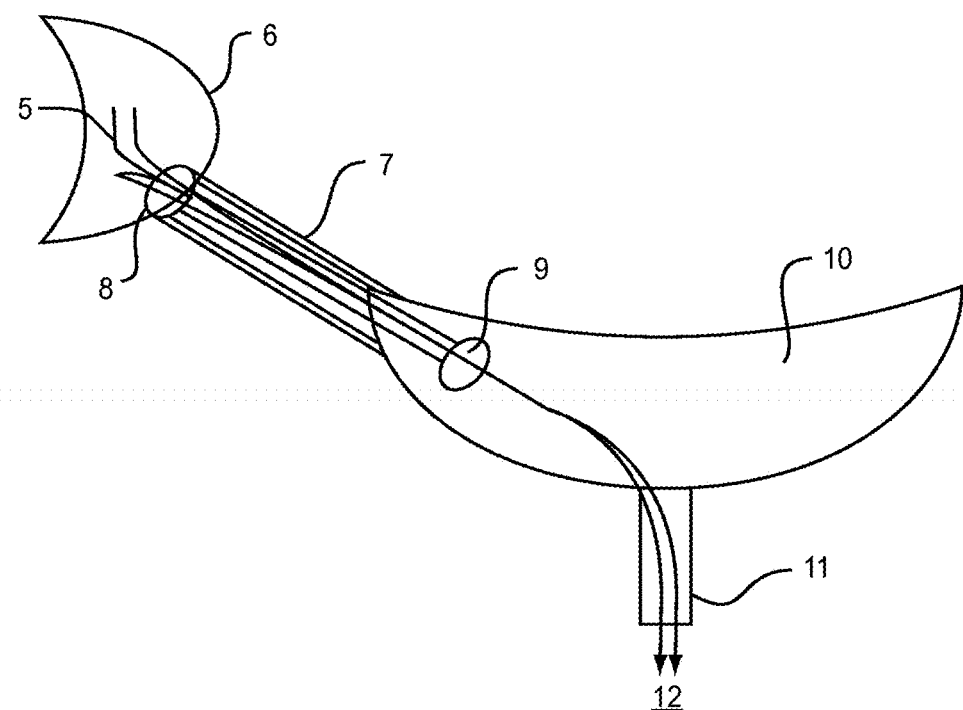
FIG. 2 is an example of the invention as applied to stenting a Ureter with predominate anchorage at distal ends in the bladder and kidney respectively maintaining placement location.

Referring now to the drawings, particularly in FIG. 1, there is generally indicated the stent of the present invention. As illustrated in FIG. 1, the body of the stent 1 is displayed, along with the ureteral lumen 3 and the outward radial forces 2. The trumpet or barbell distal end for anchorage with radiopacifier fill 4 is also shown. In FIG. 2, the path urine travels through the body is shown. How the urine 5 will flow from the kidney, 6 through the anchorage in the kidney, 8 through the ureter, 7 through the anchorage of the ureter 9 and into the bladder 10. The urine will then flow 12 through the urethra 11.

Figure 3:
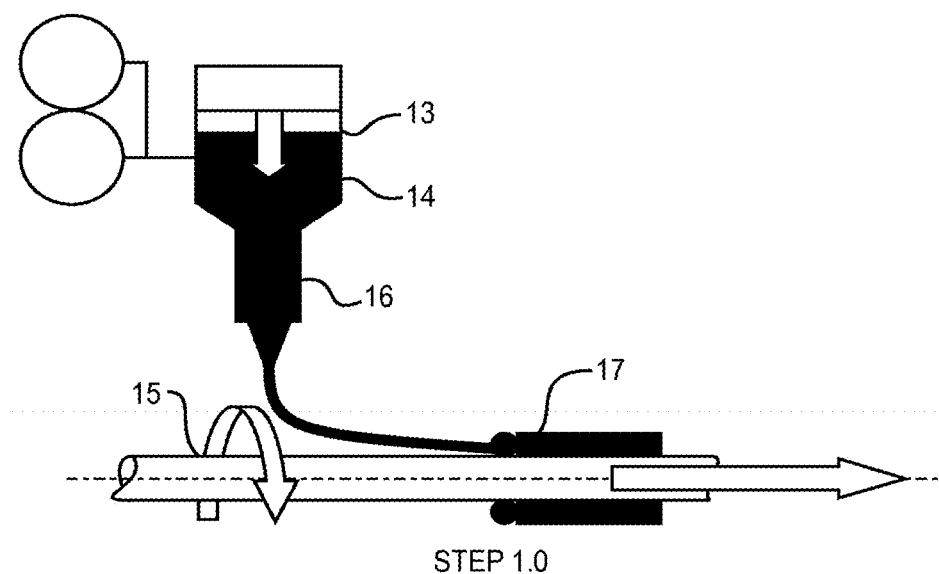
FIG. 3, step (1) discloses the basic function of the process whereby after depositing the first layer, that deposition is rinsed with water essentially coagulating the hydrogel in places on the mandrel. Then the hydrogel component is rinsed and then dried either on mandrel, or can be removed from mandrel and exchanged to a smaller or larger mandrel for an additional effect. Thereafter a concurrent layer can be added.
Figure 3:
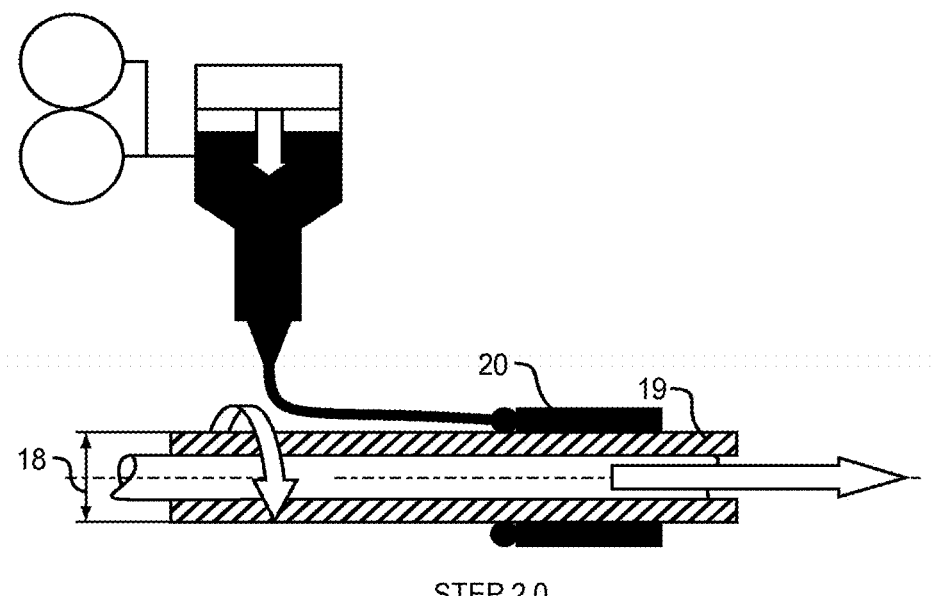

FIG. 3 displays the process of making the hydrogel stent. In step 1, the composition of the hydrogel 13 that is desired is passed through the syringe body or reservoir 14 and subsequently through a needle 16 to form the first layer 17 which will be held in place by the mandrel 15. In step 2, the process is repeated to form the second layer 20 around the first layer 19 and both held in place by the mandrel.

Figure 4D:
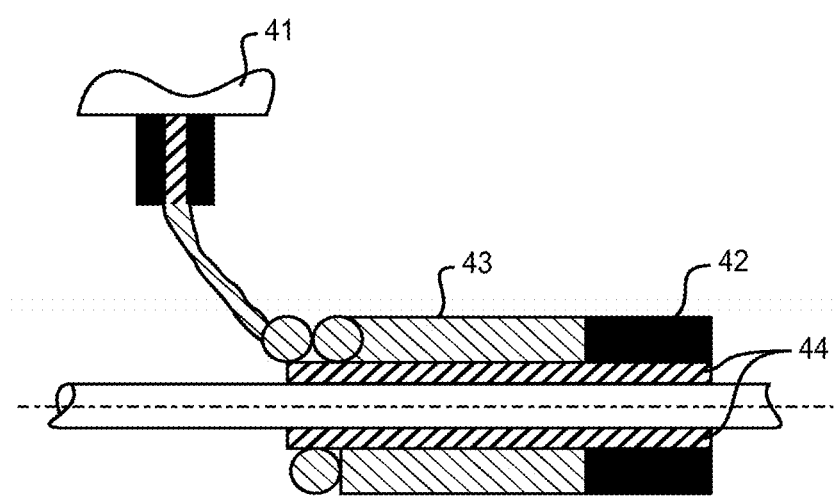

FIG. 4A the front view of the stent producing process. The adjustable process parameters of temperature, pressure and viscosity 21 and a reservoir of hydrogel in solvent solution 23 then the variable of process parameter flow rate 22. This will then go through the manifold outlet diameter 24 that allows for stents of various diameters to be created. The length of the stent can also be varied by the distance deposition filament 26. The mandrel RPM or line speed 25 can be varied and multiple stents can be received by the multiple mandrels 27. FIG. 4B shows the side view of the stent producing process. The reservoir of material 28 goes through the Outlet ID 30 which travels through a set distance 29 of the length of stent where a lead dimension is set 31. The mandrel 32 will hold a set deposition thickness 35 while rotating a set RPM 33 and coming out of the process at a certain line speed 34. FIG. 4C shows the end view of the stent producing process with reservoirs of material A 36 and material B 37. These two materials then flow through the flow direction valve 38. A mandrel 39 then holds in place where the deposition 40 will come from. FIG. 4D shows a side view from the opposite side of 4B shows the reservoir of material 41 with a material A 42 and material B 43 that make up the inner layer of the stent 44.

FIG. 5A shows how the second layer will be attached to the first with a Mandrel dimension A 45 holding in place the subsequent outer layer 46 around the inner layer 47 with a variable mandrel length 48 and a mandrel dimension B 49. FIG. 5B shows the two step process of how the mandrel holds the structure of the stent as it comes through. In step 1, the variable mandrel diameter 53 with a deposit layer on the mandrel 50 is then dehydrated 51 onto a mandrel 88. The second step to create a smaller diameter stent is shown in step 2 with a smaller mandrel 54 with a smaller dehydrated stent 52.

Figure 7B:
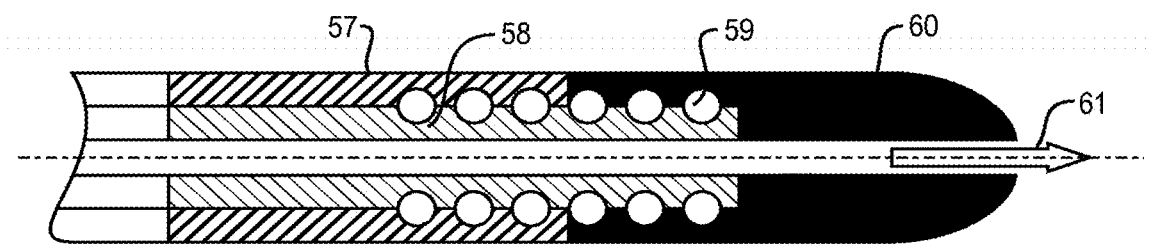
Figure 7C:
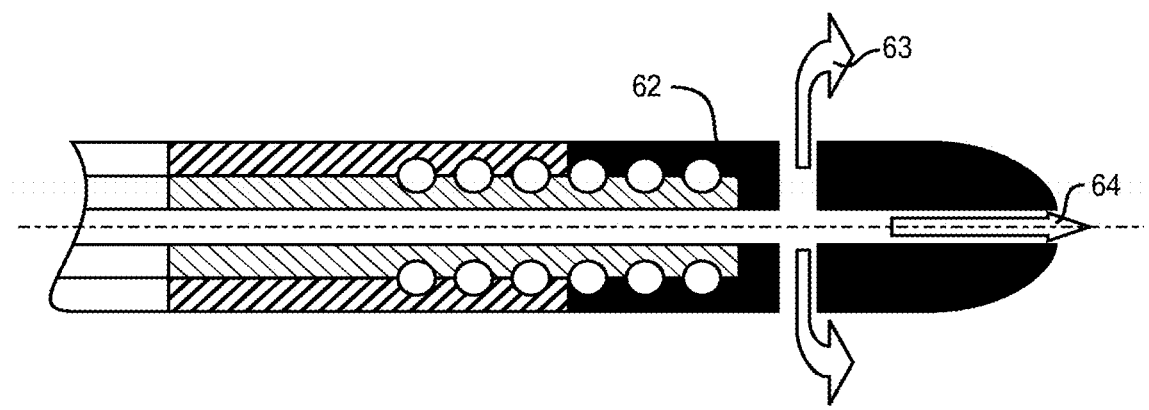
Figure 7D:
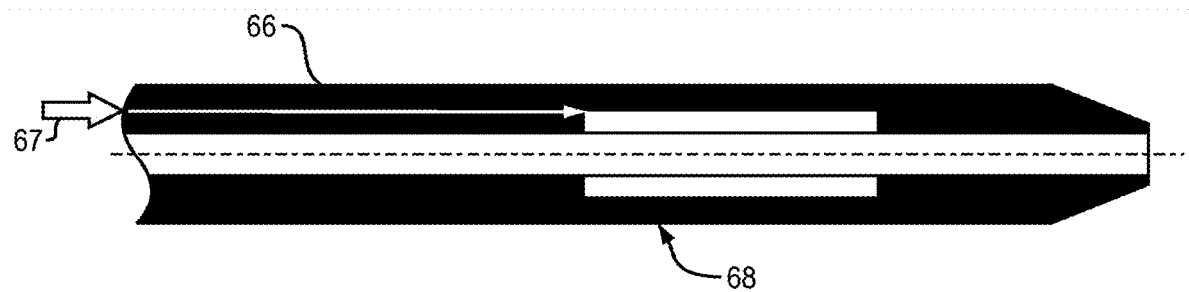

FIG. 6 is a graph depicting how much the stent can stretch based on the weight of the load applied to it. FIG. 7A shows a view of what the end of a finished structural hydrogel device 55 would look like with an embedded weave composition 56 of the final stent. FIG. 7B shows a cross section of the finished stent with an inner layer 58, an outer layer 57 a coil form 59 and a hydrogel tip 60. The flow of fluid through the stent is also shown 61. FIG. 7C shows the same cross section with a variable diameter of both the inner layer 63 and the outer layer 62 with the same outward flow 64. FIG. 7D shows how a catheter or stein can possibly be filled with medication that will flow into the bloodstream when the bloodstream has a lower concentration than the catheter or stent.

Figure 7E:
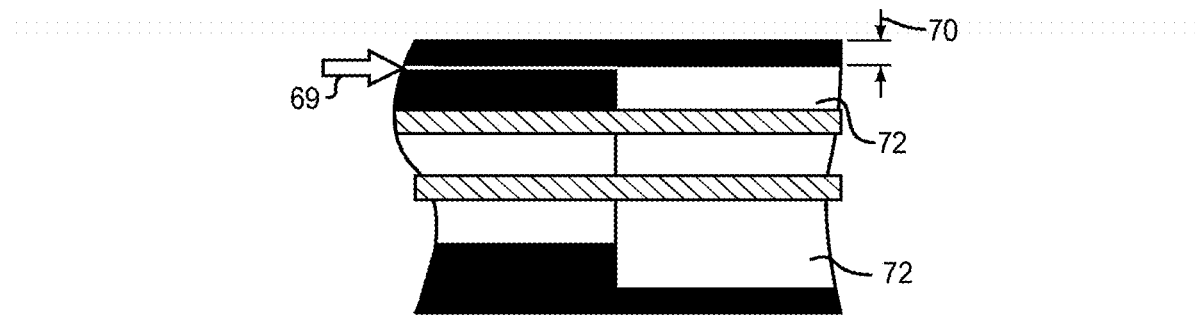
Figure 7F:
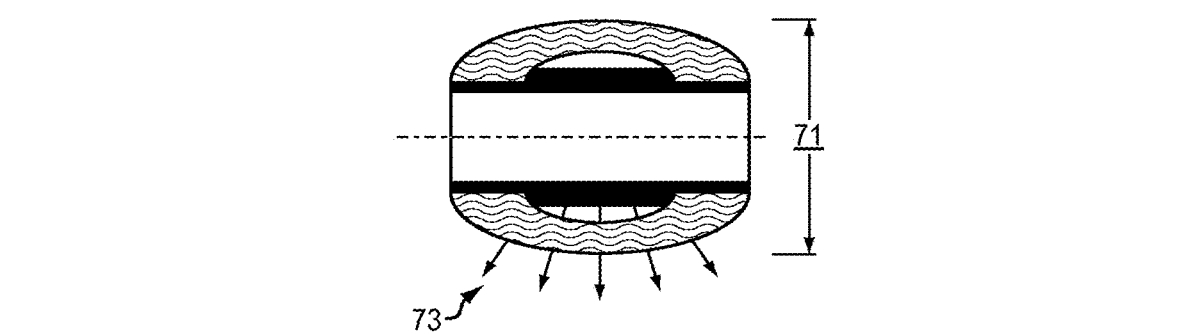
Figure 7G:
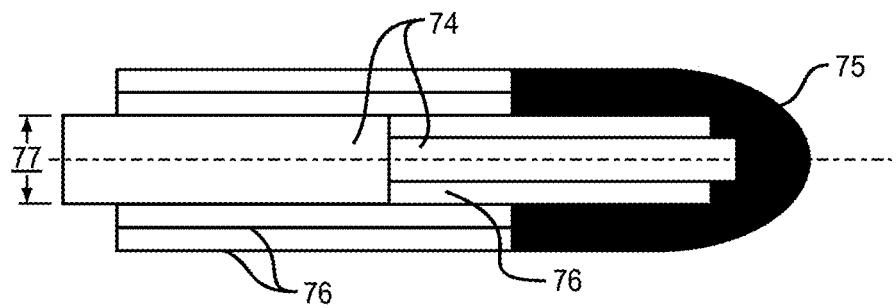

The potential inflation of the outer layer 67 of the catheter shaft 66 of a low profile integral balloon 68 is displayed. FIG. 7E shows a more detailed side view of the potential expansion for drug refilling purposes. The optional inflation 69 with a thin wall of the balloon 70 with an optional drug reservoir 72 is shown more clearly. FIG. 7F shows an end view of what the catheter or stent will look like when expanded. The increased diameter of the stent 71 with the force that is exerted outwards by the fluid flowing through 73 is displayed. FIG. 7G shows what the ends of the devices will look like if expanded. A solid core 74 with multiple layers of radiopaque filled hydrogel forming a tip 75 with the layers required by the process 76. A potential adhesive 77 could also be implemented. FIG. 8A shows three potential configurations of A 78, B, 79 and C 80.

Figure 8B:
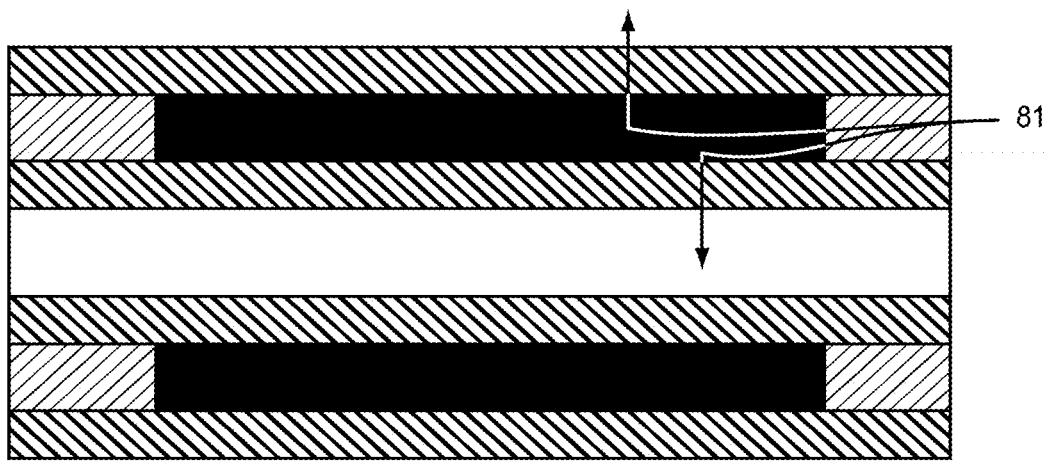

These configurations depict different potential forces that may he applied depending on the volume and amount of flow of liquid through the device. FIG. 8B shows how drugs may be delivered through diffusion 81 if that option is pursued. FIG. 9A shows an interior cross sectional view of the final device while FIG. 9B shows what the outside of the final device will look like.

FIG. 10 shows the variable diameters of the outer layer with the interior diameter 83 and exterior diameter 84 when the device is fully hydrated 86. The same is shown for the inner layer with the interior diameter 85 and the exterior diameter 84 when the device is fully hydrated 87.

In the preferred embodiment, a physician skilled in the ability can be expected to implant and retrieve a Structural Hydrogel Device in the same manner as a thermoplastic device. A Structural Hydrogel Ureteral Stent or catheter can be implanted trans-urethrally or percutaneously from the kidney into the Ureter considerably smaller in diameter and once wetted immediately lubricous while hydrating, and increasing in corresponding volume.

This instant process ideally can be used to fabricate an entity, device or product which exhibits a reversible function, ideally infinitely where the material can be dehydrated and re-hydrated as required. In that sense, the primary mechanism of the process is that the first or inner layer material is deposited fully hydrated and then subsequently dehydrated as a part of the process, see step (1) FIG. 3, FIGS. 4A & B. Then a sequential layer is added whereby the solvent in the second layer solution that allows the hydrogel to be in a semi-liquid phase will interact with the dehydrated first or inner layer beneath and a covalent interface will be achieved, see step (2) FIG. 3, FIGS. 4A & B. This material defined as a hydrogel, is in its semi-fluid phase before solidification, and used as a raw material in the disclosed process. Furthermore different concentrations of solids or fillers in the hydrogel material can be deposited by for example controlling several reservoirs flowing into one manifold with one unique outlet, see FIGS. 4C & D.

Additionally, mandrels used for initial processing, may be removed to create additional effects. For example a larger OD mandrel will result in a thinner dehydrated wall when preparing for a concurrent layer. Similarly, a smaller OD mandrel, no mandrel or a combination of diameters could be used for additional desired effects, see FIGS. 5A & B.

Conversely, the disclosed (reversible dehydration/hydration lamination) process provides a novel advantageous alternative when designing or fabricating products made from raw materials such as hydrolyzed PAN type materials that need to exhibit excellent mechanical characteristics while maintaining low percent solids, see FIG. 6.

One of the most valuable attributes of the disclosed process allows processing from solvent-based hydrogel solutions that result in a structural hydrogel device exceeding the performance of coagulated hydrolyzed PAN products and components. Therefore the disclosed process exceeds the limitation of materials such as hydrolyzed PAN but also includes any formulation that exhibits a reversible function whereby the material can be dehydrated and re-hydrated. In that manner, the disclosed process allows the layering and or lamination of layers in accordance with the disclosed process resulting in a laminated structural hydrogel of predominately low solids and high corresponding aqueous content that will exhibit significant mechanical characteristics such that a stable product can be produced. Subsequently, this novel process allows the lamination of subsequent concurrent layers that in a final configuration provide the enhanced mechanical characteristics that result in 100% structural hydrogel products as well as hybrid versions, see FIGS. 7A, B, C, D, E, F & G.

Although one primary advantage of the disclosed process is the ability to adhere one hydrogel layer to another hydrogel layer or other surface material, and that the lamination of such layers together results in and benefit from the compression of the outer layers or at least the integration of the outer layer to the associated inner layer; one can incorporate or produce a hybrid by for example incorporating a braid or fabric between layers, see FIG. 7A.

Therefore the disclosed process results in the revolutionary never before claim of adhering one hydrogel layer to another hydrogel layer, which as disclosed is the primary influence resulting in the superior mechanical and biocompatibility performance characteristics of the as called structural hydrogel product or device.

A hybrid device for example utilizing a structural hydrogel distal tip manufactured in accordance with the disclosed process, and adhered to or processed directly onto a conventional metal, TPE/TPU device surface, such as for example a catheter where the hydrogel is not a coating but an integral component, see FIGS. 7B & C could diminish complications related to implantation.

Furthermore, a hybrid device utilizing a structural hydrogel design manufactured in accordance with the disclosed process can be engineered with different percent concentrations of solids in a specific layer, or segmented or positioned specifically along the axis of a catheter shaft for example. In this manner radiopaque media can be placed where it is desired, or a denser matrix can be produced in specific layers or segment along the axis, providing a differential gradient that would promote diffusion or conduction enhancing drainage, or providing a specific drug delivery barrier, see FIGS. 8A & B.

Otherwise, current processing of hydrolyzed PAN and alike hydrogels is limited to only primarily coagulation of freely poured or molded gel, typically into a sheet form where further processed including secondary operations that include many methods of cross-linking such as exposure to radiation, freeze/thaw methods, and modifications to the polymer chemistry, as well as using hot acid to enhance its hydrophilicity and or primers that are required to attach coatings to an intended substrate.

This dangerous, expensive and marginally successful operation is not required with the disclosed process which produces a low solids and therefore correspondingly highly hydrophilic product.

Thermoplastic extrusion processes are possible with many hydrogel formulae, in order to make them perform like conventional TPE and TPU's. Although thermoplastic extrusion typically results in components and products that exhibit adequate mechanical characteristics, thermoplastic extrusion of for example hydrolyzed PAN does not yield a component or product that exhibits a large aqueous content compared to product manufactured from the disclosed process. Furthermore, for example extruding hydrolyzed PAN requires loading the polymer resin with large amounts of plasticizers, and when radiopacifers are added the end product contains a much higher percent of solid than exhibited by products manufactured with the disclosed process, diminishing the hydrophilicity, and bio-compatibility.

The advantages therefore are that the disclosed process which doesn't require thermoplastic processing (although it can be extruded or molded); doesn't require post processing to enhance hydrophilicity, and isn't sensitive to variations in the base polymer chemistry can be used to cost effectively derive products which will exhibit a much higher level of aqueous absorption and related bio-compatibility, which is paramount and related while exhibiting the required mechanical characteristics, which if not achieved, the device or product application wouldn't be possible.

To achieve this bio-compatibility and in accordance with the benefits of the disclosed process a catheter for example might be produced with several layers whereby the last layer is void of but all previous layers would be filled with radiopacifiers, see FIG. 9. In this manner human tissue does not come into contact with the radiopaque filler medias as would devices produced of or conventional hydrogels, TPE or TPU's.

Also drug delivery systems and attempts to force the change in volume resulting in for example predetermined radial forces can be exhibited by adding or not adding fillers or generally the specification of the percent of hydrogel solids in a given layer or layers as illustrated in FIG. 8.

FIG. 11 is a flow chart of a method 1100 according to an embodiment. In step 1101, an inner layer material comprising and/or consisting of a hydrogel is deposited on a rotating, horizontally-disposed mandrel (e.g., mandrel 15). In step 1102, the inner layer is coagulated in place on the mandrel. In step 1103, the inner layer is dehydrated. In step 1104, a second layer of material comprising and/or consisting of a hydrogel is deposited on the dehydrated inner layer from step 1103 to form a medical device, which can be a stent, a catheter, a plug, a profile plug, a component, a profile, a segment, an occultation device, a slug, a drug-delivery apparatus, a self-closing cylinder, or another medical device (e.g., having another shape or geometry) (in general, a medical device). The medical device is formed without thermoplastic processing, as described above.

In step 1105, the medical device is placed in a solution having an osmolarity approximately equal (e.g., within about 20%, within about 10%, and/or within about 5%) to the osmolarity of a target body fluid in a target anatomical site. As used herein, "about" means plus or minus 10% of the relevant value. Also, as used herein, "% NaCl" refers to the concentration (in g/mL) of NaCl in water, which is preferably deionized water. For example, a 3% NaCl saline has a concentration of 0.03 grams of NaCl per milliliter of water. In an embodiment, the solution can comprise a saline solution in a range of about 3% NaCl to about 4% NaCl, including about 3.5% and any value or range between any two of the foregoing percentages.

In step 1106, the medical device absorbs the solution, which expands the physical dimensions of the medical device. These physical dimensions can be referred to as the pre-implantation physical dimensions of the medical device.

After step 1106, the medical device is implanted (or placed) in the target anatomical site in step 1107. In step 1108, some or all of the physical dimensions of the medical device remain about the same (e.g., +/−10%) after the medical device is implanted compared to the pre-implantation physical dimensions (e.g., the physical dimensions of the medical device after it was placed in the hypertonic saline solution). For example, the outer diameter, the inner diameter, and/or the length of the medical device can remain about the same after the medical device is implanted compared to the pre-implantation physical dimensions. An example of a target anatomical site and target body fluid include the bladder or ureter where the target body fluid is urine. Another example of a target anatomical site includes a vein of a diabetic patient where the target body fluid is blood with a high glucose concentration.

It is noted that this method is also applicable to placing or implanting the medical device in another fluid environment (e.g., a marine environment). In general, the medical device can be pre-treated in a solution having an osmolarity that is approximately the same as the osmolarity of the target fluid or liquid in the target environment. Without being bound by theory, it is believed that the space occupied by the solute particles (e.g., salt such as NaCl) contributes to maintaining stable mechanical characteristics and physical dimensions because no net exchange of solute particles is likely with the target environment (e.g., the medical device and the target environment are approximately balanced with respect to solute concentration) and/or if there is a net exchange of solute particles, the medical device is sized appropriately for after taking on the environmental fluid in which it is placed.

FIG. 12 is a flow chart of a method 1200 for manufacturing a medical device according to another embodiment. Steps 1101-1104 are the same as in method 1100. In step 1205, the medical device is placed in a solution (e.g., a saline solution) having an osmolarity that is different than the osmolarity of a target body fluid in a target anatomical site. More generally, the osmolarity of the solution is different than the osmolarity of a target environment, which can be a body fluid or another fluid/liquid. In step 1206, the medical device absorbs the solution, which expands the physical dimensions of the medical device. These physical dimensions can be referred to as the pre-implantation physical dimensions of the medical device.

After it is placed in the saline solution, the medical device can be implanted in the target anatomical site in step 1207. In step 1208, some or all of the physical dimensions of the medical device change (increase or decrease) after the medical device is implanted compared to the pre-implantation physical dimensions. For example, the outer diameter, the inner diameter, and/or the length of the medical device can change (increase or decrease) after the medical device is implanted compared to the pre-implantation physical dimensions.

When the osmolarity of the solution is lower than the osmolarity of the target body fluid, some or all of the physical dimensions decrease (e.g., within a range of about 20% to about 30%) compared to the pre-implantation physical dimensions. An example of a solution with a lower osmolarity than the target body fluid is pure deionized water and a saline solution of about 0.1% NaCl to about 2.5% NaCl, including about 0.5% NaCl, about 0.9% NaCl (sometimes referred to as normal 0.9% saline), about 1% NaCl, about 1.5% NaCl, about 2% NaCl and any value or range between any two of the foregoing percentages. An example of a target anatomical site and target body fluid include the bladder or ureter where the target body fluid is urine. Other example target body fluids can include blood (e.g., of a diseased or healthy patient), cerebrospinal fluid (e.g., in spine or brain), fluid in the digestive system, etc. in another example, the target environment can comprise seawater (which may vary regionally such as in the North Atlantic and in the Mediterranean), fresh water, etc.

An application of having smaller post-implantation physical dimensions is a self-closing cylinder. The cylinder can have a small internal diameter that can be used to insert a guidewire during implantation. After the cylinder is implanted, the internal diameter decreases to become closed or substantially closed, which transitions the self-closing cylinder to a slug or solid.

When the osmolarity of the solution is higher than the osmolarity of the target body fluid (or target environment), some or all of the physical dimensions increase (e.g., within a range of about 20% to about 30%) compared to the pre-implantation physical dimensions. An example of a solution with a higher osmolarity than the target body fluid is a hypertonic saline solution having more than 4% NaCl, such as a range of about 4% NaCl to about 9% NaCl, including about 5% NaCl, about 6% NaCl, about 7% NaCl, about 8% NaCl, and any value or range between any two of the foregoing percentages. In some embodiments, the range includes about 4% NaCl to about 5% NaCl, about 4.5% NaCl to about 5.5% NaCl, about 4% NaCl to about 6% NaCl, or another range. An example of a target anatomical site and target body fluid include the bladder or ureter where the target body fluid is urine. Other example target body fluids can include blood (e.g., of a diseased or healthy patient), cerebrospinal fluid (e.g., in spine or brain), fluid in the digestive system, etc. in another example, the target environment can comprise seawater (which may vary regionally such as in the North Atlantic and in the Mediterranean), fresh water, etc.

FIG. 18 is an example table 1800 of the change in physical dimensions of the medical device when it is saturated (e.g., pre-treated) in a first solution having a first osmolarity and then placed in a second solution having a second osmolarity. In general, when the osmolarity of the first solution is approximately equal to the osmolarity of the second solution, the physical dimensions of the medical device are about the same when the medical device is placed in the second solution compared to the physical dimensions of the medical device after it is saturated in the first solution. In addition, the medical device shrinks when the first solution has a lower osmolarity than the second solution. That is, when the first solution has a lower osmolarity than the second solution, the physical dimensions of the medical device decrease when the medical device is placed in the second solution compared to the physical dimensions of the medical device after it is saturated in the first solution. Further, the medical device expands (e.g., swells) when the first solution has a higher osmolarity than the second solution. That is, when the first solution has a higher osmolarity than the second solution, the physical dimensions of the medical device increase when the medical device is placed in the second solution compared to the physical dimensions of the medical device after it is saturated in the first solution.

Table 1800 also illustrates the effect of a pH change between the first and second solutions. In general, increasing the pH from the first solution to the second solution causes the medical device to expand. For example, when the first solution has a lower pH than the second solution, the physical dimensions of the medical device increase when the medical device is placed in the second solution compared to the physical dimensions of the medical device after it is saturated in the first solution. Likewise, decreasing the pH from the first solution to the second solution causes the medical device to shrink. For example, when the first solution has a higher pH than the second solution, the physical dimensions of the medical device decrease when the medical device is placed in the second solution compared to the physical dimensions of the medical device after it is saturated in the first solution.

Table 1800 can be used to determine a desired outcome (e.g., swell, shrink, or no change of medical device physical dimensions) based on a known target environment (e.g., target body fluid) for the medical device. For example, if we know the target body fluid (e.g., patient's urine) exhibits a first osmolarity and/or a first pH, we can first saturate the medical device in a solution having a second osmolarity and/or a second pH to achieve the desired outcome. The first and second osmolarities and/or pHs can be approximately matched to achieve stability in the medical device physical dimensions. Alternatively, an appropriate difference in osmolarity and/or pH, between the saturating solution (first solution) and the target body fluid (the second solution), can be selected to achieve a desired increase or decrease in medical device physical dimensions with respect to the medical device physical dimensions when saturated in the saturating solution (first solution). For example, when the medical device is used to deliver a medication, such as an antibiotic in aqueous solution having a pH of about 8, we could specify that the aqueous pharmaceutical be mixed with a specific % NaCL saline such that when implanted the device remains stable, shrinks (increases delivery rate), or expands if appropriate.

It is noted that this method is also applicable to placing or implanting the medical device in another fluid environment (e.g., a marine environment). In general, the medical device can be pre-treated in a solution having an osmolarity that is different than the osmolarity of the target fluid or liquid in the target environment to achieve a desired increase or decrease in the physical dimensions of the medical device after it is placed in the target fluid or liquid.

In other embodiments, the physical dimensions of the medical device can change pre- and post-implantation when the pH changes. For example, increasing the pH from pre-implantation (e.g., in a first fluid having a first pH) and post-implantation (e.g., in a second fluid having a second pH that is higher than the first pH) causes some or all of the physical dimensions of the medical device to increase (e.g., up to a range of about 20% to about 30% depending on the difference in pH) compared to the pre-implantation physical dimensions of the medical device. Conversely, decreasing the pH from pre-implantation (e.g., in a first fluid having a first pH) and post-implantation (e.g., in a second fluid having a second pH that is lower than the first pH) causes some or all of the physical dimensions of the medical device to decrease (e.g., up to about 20% to about 30% depending on the difference in pH) compared to the pre-implantation physical dimensions of the medical device. The physical dimensions of the medical device can increase or decrease in a reversible manner by placing the medical device in solutions having different pHs so long as the pH is greater than or equal to about 4.5. Without being bound by theory, it is believed that a change in pH can cause a change in hydrolysis of the medical device, which can cause the physical dimensions change.

FIG. 13 is a flow chart of a method 1300 for manufacturing a medical device according to another embodiment. Steps 1101-1104 are the same as in method 1100. In step 1305, the medical device is placed in a liquid (e.g., water) that includes a therapeutic agent that can be dissolved or suspended. The therapeutic agent can comprise a drug or pharmaceutical (e.g., an antibiotic, a hormone, etc.), a vitamin or mineral, a chemotherapy agent or drug, and/or another therapeutic agent. The hydrogel material in the medical device absorbs the therapeutic agent in step 1306.

After the medical device is manufactured, it can be implanted into a target anatomical site in step 1307. The implanted medical device will then release (e.g., desorb and/or diffuse) some or all of the therapeutic agent in step 1308. For example, the therapeutic agent can equilibrate between the medical device and the target anatomical site such that there are approximately equal concentrations of the therapeutic agent in or on the hydrogel material and in the target anatomical site. This may result in the hydrogel material releasing substantially all (e.g., about 99%) of the therapeutic agent to the target anatomical site.

An antibiotic can have a pH of about 8, which can cause the medical device to swell (e.g., increase in physical dimensions). In some embodiments, the antibiotic can be placed in a solution (e.g., a saline solution) having a higher osmolarity than the target body fluid in the target anatomical site, which would promote a decrease in post-implantation physical dimensions of the medical device. The combination of the swelling caused by the high pH and the shrinking caused by the high-osmolarity solution can result in a net of about no change (e.g., +/−10%) of the physical dimensions of the stent compared to its pre-implantation physical dimensions.

FIG. 14 is a flow chart of a method 1400 for manufacturing a medical device according to another embodiment. Steps 1101-1104 are the same as in method 1100. In step 1405, a selective membrane can be placed on the medical device prior to implantation. The selective membrane can be selective for one or more target molecules that may be in a target body fluid in a target anatomical site. For example, the selective membrane only allows the target molecule(s) to pass through the membrane to the surface of the medical device. Alternatively, a filter can be attached to the medical device. In another embodiment, the medical device can function as a selective membrane (e.g., by selectively absorbing the target molecule(s)) with or without having a selective membrane or filter attached to the medical device.

In step 1406, the medical device is implanted in the target anatomical site where the medical device is disposed in a target body fluid. In step 1407, the medical device selectively absorbs the target molecule(s) until equilibrium is reached between the target molecule(s) concentration in the target body fluid and the target molecule(s) concentration in the medical device (e.g., in the hydrogel). The medical device can be replaced when at or near the time that equilibrium has been reached. In one example, the selective membrane can be selective for magnesium and/or calcium oxalate in the urinary system. Removing magnesium and/or calcium oxalate from the urinary system can reduce the likelihood of kidney (renal) stones from forming. In another embodiment, the selective membrane can selectively allow undesirable components of blood to pass through and abord in the medical device to perform hemodialysis. In another example, the selective membrane can be selective for glucose in the blood stream.

In some embodiments, one or more of methods 1100, 1200, 1300, and/or 1400 can be combined. For example, the medical device can be pre-treated in a solution that includes a predetermined osmolarity (e.g., as in methods 1100, 1200) and that includes a therapeutic agent (e.g., as in method 1300).

FIG. 15 is a block diagram of an apparatus 1500 for manufacturing a medical device according to an embodiment. The apparatus 1500 can be used with any of methods 1100, 1200, 1300, and/or 1400. The apparatus 1500 includes a receptacle or container or vessel 1510 that retains a fluid or liquid 1520. The fluid or liquid 1520 can have a predetermined osmolarity and/or can include a therapeutic agent. A fluid having a predetermined osmolarity can include a saline solution in the range of about 0.1% NaCl to about 8% NaCl, as described above. A medical device 1530, such as any of the medical devices described herein, can be placed in the fluid or liquid 1520 for pre-treatment prior to implantation.

FIG. 16 is a block diagram of a medical device 1600 that can selectively-absorb one or more target molecules according to an embodiment. The medical device includes a catheter or stent 1610 and a selective membrane 1620. The selective membrane 1620 is attached to the catheter or stent 1610. The selective membrane 1620 can selectively allow one or more target molecules to pass through the selective membrane 1620 to the catheter or stent 1610. For example, the selective membrane 1620 can selectively allow magnesium, that may be in the urine, to pass through to be absorbed in the hydrogel material of the catheter or stent 1610, which can reduce the likelihood of kidney stones. In an alternative embodiment, the catheter or stent 1610 can function as a selective membrane with or without having a selective membrane 1620 or filter attached to the catheter or stent 1610.

In another embodiment, a dehydrated or partially-hydrated medical device can expand (e.g., increase in physical dimensions) to a predetermined size after it is placed or implanted in the body (e.g., in a body fluid). For example, a dehydrated or partially-hydrated medical device can be placed in the brain 1700 to fill an aneurism 1710 using a small segment of this dehydrated or partially-hydrated medical device 1720 with the anticipation that it will absorb blood and swell to a predetermined size or profile 1730, for example as illustrated in FIGS. 17A and 17B. FIG. 17A illustrates the implanted stent in a dehydrated or partially-hydrated state. FIG. 17B illustrates the implanted stent after it has hydrated (e.g., in a fully-hydrated state) and conformed to the profile 1730. A dehydrated or partially-hydrated medical device can be placed in another target anatomical site to swell to a predetermined size as desired.

It is noted that the catheter or stent can be formed of different grades of material which can have different characteristics such as swell, tensile modulus, etc. The more hydrophilic the material grade, the more swell, because a high volume of aqueous media is absorbed. However generally speaking rates of absorption/diffusion are similar between the material grades which would indicate a lower modulus, softer higher swell variation of the polymer might benefit from a hypertonic saline when a stiffer less swell variation may not. That understood a stiffer less swell variation will still benefit from being balanced with the appropriate osmolarity, managed by salinity, as the environment it is intended for (e.g., the target body fluid in the target anatomical site).

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

The invention claimed is:

1. A method for manufacturing a medical device, comprising:
    depositing an inner layer material comprising a hydrogel on a rotating, horizontally-disposed mandrel;
    coagulating the inner layer material comprising the hydrogel in place on the mandrel;
    dehydrating the inner layer material;
    depositing a second layer of material comprising a hydrogel on the inner layer material such that the medical device is produced without thermoplastic processing; and
    placing the medical device in a solution having a predetermined osmolarity.

2. The method of claim 1, wherein the predetermined osmolarity is approximately equal to an osmolarity of a target body fluid, whereby one or more physical dimensions of the medical device remains about the same after the medical device is implanted in a target anatomical site that includes the target body fluid.

3. The method of claim 2, wherein the solution comprises a hypertonic saline solution.

4. The method of claim 3, wherein the hypertonic saline solution has an NaCl concentration is in a range of about 3.5% NaCl to about 4% NaCl.

5. The method of claim 4, wherein the target body fluid comprises urine.

6. The method of claim 2, wherein the one or more physical dimensions comprises an outer diameter of the medical device.

7. The method of claim 1, wherein the predetermined osmolarity is greater than an osmolarity of a target body fluid, whereby one or more physical dimensions of the medical device increases after the medical device is implanted in a target anatomical site that includes the target body fluid.

8. The method of claim 7, wherein the solution comprises a hypertonic saline solution having an NaCl concentration in a range of about 4% NaCl to about 5% NaCl.

9. The method of claim 8, wherein:
    the one or more physical dimensions comprises an outer diameter of the medical device, and
    the outer diameter increases by about 20% to about 30% after the medical device is implanted in the target anatomical site compared to the outer diameter immediately before the medical device is implanted in the target anatomical site.

10. The method of claim 1, wherein the predetermined osmolarity is lower than an osmolarity of a target body fluid, whereby one or more physical dimensions of the medical device decreases after the medical device is implanted in a target anatomical site that includes the target body fluid.

11. The method of claim 10, wherein the solution comprises a saline solution having an NaCl concentration in a range of about 0.1% NaCl to about 2.5% NaCl.

12. The method of claim 11, wherein:
    the one or more physical dimensions comprises an outer diameter of the medical device, and
    the outer diameter decreases by about 20% to about 30% after the medical device is implanted in the target anatomical site compared to the outer diameter immediately before the medical device is implanted in the target anatomical site.

* * * * *